(12) United States Patent
Etchin et al.

(10) Patent No.: US 9,523,634 B1
(45) Date of Patent: Dec. 20, 2016

(54) CENTERING HOLDER FOR OPTICAL INTERROGATION

(71) Applicant: TruTag Technologies, Inc., Kapolei, HI (US)

(72) Inventors: Sergey Etchin, Castro Valley, CA (US); Timothy Learmonth, Berkeley, CA (US); Michael P. O'Neill, Kaneohe, HI (US); Christopher Perrott, Edinburgh (GB); David Shepherd, Edinburgh (GB); Christopher Tacklind, Menlo Park, CA (US)

(73) Assignee: TruTag Technologies, Inc., Kapolei, HI (US)

( * ) Notice: Subject to any disclaimer, the term of this patent is extended or adjusted under 35 U.S.C. 154(b) by 0 days.

(21) Appl. No.: 14/723,014

(22) Filed: May 27, 2015

(51) Int. Cl.
*G01N 21/01* (2006.01)
*G01N 21/13* (2006.01)
*G01N 21/11* (2006.01)

(52) U.S. Cl.
CPC .............. *G01N 21/13* (2013.01); *G01N 21/11* (2013.01)

(58) Field of Classification Search
CPC ................................ G01N 21/03; G01N 21/05
See application file for complete search history.

(56) References Cited

U.S. PATENT DOCUMENTS

| | | | |
|---|---|---|---|
| 4,544,800 A | 10/1985 | Katsuura | |
| 4,610,524 A | 9/1986 | Ruhl | |
| 5,032,011 A * | 7/1991 | Muchel | G02B 21/12 359/385 |
| 7,738,193 B2 * | 6/2010 | Weber | G02B 7/023 359/811 |
| 8,342,408 B2 | 1/2013 | Biss et al. | |
| 2001/0001574 A1 * | 5/2001 | Baer | G01N 1/2813 356/244 |
| 2006/0028641 A1 * | 2/2006 | Frank | G02B 21/26 356/244 |
| 2008/0174773 A1 * | 7/2008 | Mark | G01N 21/01 356/244 |
| 2010/0302534 A1 * | 12/2010 | Watanabe | G01N 35/00 356/246 |

OTHER PUBLICATIONS

Thorlabs. Kinematic Self-Centering Mount. http://www.thorlabs.us/newgrouppage9.cfm?objectgroup_id=6214. Printed on May 12, 2015.
Thorlabs. Kinematic Bases. http://www.thorlabs.us/newgrouppage9.cfm?objectgroup_id=1546.Printed on May 12, 2015.

* cited by examiner

*Primary Examiner* — Michael P Stafira
(74) *Attorney, Agent, or Firm* — Van Pelt, Yi & James LLP

(57) ABSTRACT

A sample holder comprises a bottom and one or more arms. The bottom has an initial area for supporting a sample. The one or more arms actuate to move the sample in the initial area to a target area, wherein the one or more arms hold the sample.

21 Claims, 16 Drawing Sheets

CENTERING HOLDER FOR OPTICAL INTERROGATION

BACKGROUND OF THE INVENTION

A producer or reseller of items (including ingredients and components of such items)—for example a manufacturer, but also including other parties in the entire supply and distribution chain such as a supplier, a wholesaler, a distributor, a repackager, and a retailer—especially, but not limited to, high-value items, faces counterfeiting of the items. Counterfeiting includes the substitution, dilution, addition or omission of ingredients or components of the item compared to its intended product specification, as well as misrepresentation or diversion of the packaged item from its intended course of sale. This leads to loss of potential revenue as counterfeit items are sold in the place of the real item. Also, there can be health or product related damages caused by not using an authentic item as opposed to a counterfeit—for example, the counterfeit can perform differently or not at all as compared to an authentic item. This is particularly acute in industries that can affect health and safety such as industries involved with pharmaceuticals, nutritional supplements, medical devices, food and beverages, construction, transportation, and defense.

As international criminal organizations become more sophisticated, existing packaging security is proving inadequate. The complexity of many industry supply chains—for example, the supply chain of the pharmaceutical industry—lends itself to entry points for adulterated or counterfeit product(s), often found in carefully counterfeited and high-quality packaging, and sometimes in authentic packaging that has either been stolen or as part of a repackaging operation.

In complex product supply chains and markets with variable pricing, opportunities for arbitrage exist for unscrupulous parties to misrepresent product pricing without any change to the underlying product, and thus benefit monetarily, for example, as in returns, rebate or charge-back fraud. Monetary gain or loss to either side of a transaction may also result from errors in record-keeping.

In addition to counterfeiting or product misrepresentation, items that appear physically identical or similar, for example certain nutritional supplements, may actually contain different ingredients or components, but because of similar appearance may be unintentionally packaged or labeled incorrectly. Even if the items are otherwise identical, they may have different properties associated with the particular lot or batch conditions; for example, pharmaceuticals that otherwise appear identical may have different expiration dates and be incorrectly labeled due to failures or limitations in quality assurance protocols to ascertain such differences.

For product development and research, it may be beneficial at times to study and authenticate performance of items that appear identical but are made differently to learn whether or how those differences affect an end use. At times, it is important in such studies—for example in clinically masked (or 'blind') studies leading to pharmaceutical development—to be able to confidently identify the underlying item without revealing the true identity to study participants. In the case of pharmaceutical development and clinical trials, item-level identity error may be introduced, for example, at the contract research organization that repackages the various product formulations into masked unit-doses. Much time, cost, and effort goes into statistical sampling and chemical analyses to verify the true identity of the unit-doses that are ultimately administered.

In the effort to attain positive health outcomes in a more cost-effective and timely manner, healthcare providers need to focus on the adherence to health regimens, not just the efficacy of specific drugs. Understanding when, where and how often medicine is prescribed by a doctor, accurately and timely dispensed from a pharmacy, received by a patient, and consumed by the patient is helpful in understanding and verifying the effectiveness of the overall health regimen. Recording and collecting the data for appropriate analysis and study while also being able to confirm the underlying identity of the medicine at each stage is important to the reliability of the information collected.

BRIEF DESCRIPTION OF THE DRAWINGS

Various embodiments of the invention are disclosed in the following detailed description and the accompanying drawings.

DETAILED DESCRIPTION

Figure 1:
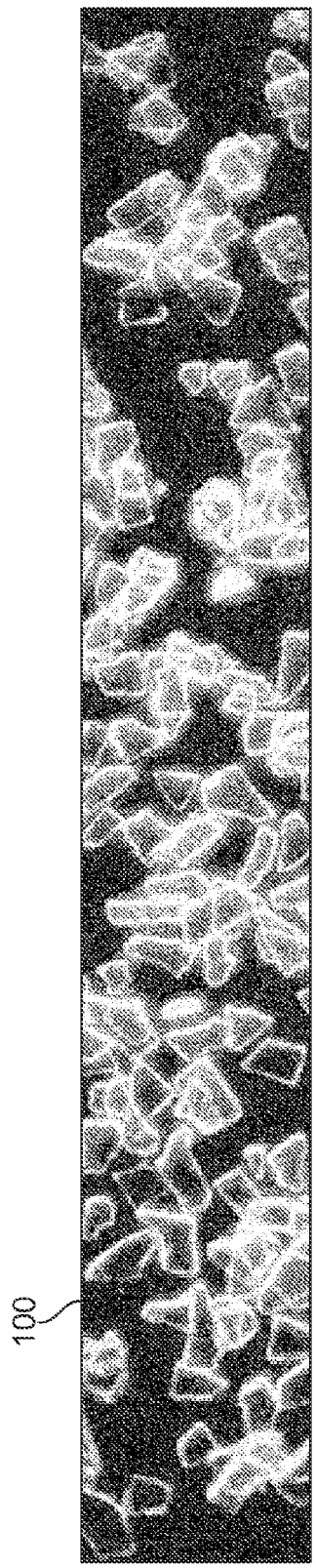
FIG. 1 is an image illustrating an embodiment of a tag.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

A system for a sample-holder for optical measurement is disclosed. The sample holder comprises a bottom and one or more arms. The bottom has an initial area for supporting a sample. The one or more arms actuate to move a sample in the initial area to a target area. The one or more arms hold the sample. In some embodiments, the sample holder comprises one or more bottom actuators, wherein the one or more bottom actuators moves the bottom to provide optical access to the sample.

In some embodiments, the sample holder sweeps a sample into a position and holds the sample. In some embodiments, the sweeping is performed with arms symmetrical in two planes (e.g., in order to accommodate typical pill shapes—for example, elliptical, oval, oblong, etc.). In some embodiments, four arms are suitable for sweeping and/or holding the sample. For example, the arms sweep and position (e.g., center) the sample for optical measurement. In some embodiments, opposite pairs of arms are driven symmetrically. In some embodiments, force on the one or more arms is largest when the arms are fully retracted—so the forces on the sample are only balanced when the opposite pairs are at the same deflection. For example, the linear force is generated using torsional springs. In some embodiments, only when the sample is held in a centered manner, then the bottom is opened to enable optical measurement. In some embodiments, the opening is large enough to easily drop a sample in and/or to be able to reach in and grab the sample using fingers to remove the sample after measurement (e.g., a thumb and a forefinger plus a sample size—for example, around 3 cm plus a sample width or length; the opening is approximately 3 cm, 4 cm, 5 cm, or 6 cm in diameter). In some embodiments, the one or more arms sweep the entire area of the well, so the sample is always captured and swept to the center. In some embodiments, the bottom area does not open the entire well area. In some embodiments, the optical measurement area comprises a small area on the surface of the sample (e.g., smaller than the surface area of the sample, smaller than the well area, etc.).

In some embodiments, the sample holder is used for holding a sample in order to make an optical measurement. The optical measuring system comprises one or more broadband sources, an optical measurement system (e.g., a spectral measurement system, an optical imaging system, etc.), and the sample holder. The one or more broadband sources are to illuminate a sample, wherein the one or more broadband sources have a short broadband source coherence length. The optical measurement system is to interrogate the sample—for example, measure a reflectance spectra or image the sample. The sample holder is to hold the sample in the correct position for illumination and reflection of light to the detector. The sample holder is designed to allow an operator to place a sample within the sample holder with low accuracy and perform a simple actuation step (e.g., a twist motion) to hold the sample at a target position with high accuracy. The sample holder additionally comprises an aperture to allow illumination light to enter and reflected light to leave the sample holder.

In some embodiments, the sample or the object is tagged so that the sample or object can be authenticated—for example, tags are applied to a pill. The tags are spectral microtags that reflect specific spectral peaks when illuminated with broadband light. The optical measurement system has a limited field of view so that the sample needs to be positioned within a target area for optical measurement. The samples need to be held in a fixed position during measurement.

In some embodiments, the optical measurement system is specifically configured to measure tags (e.g., rugate tags). In various embodiments, tags comprise one of the following materials: silicon, silicon dioxide, silicon nitride, doped silicon, or any other appropriate material. In some embodiments, tags are made of silica and deemed "generally recognized as safe"—or GRAS—by the Food and Drug Administration (FDA), rendering them biologically inert and edible. Each barely visible tag contains a custom-manufactured spectral signature chosen so as to uniquely identify or authenticate a particular product. Tags with a given spectral signature are manufactured in quantities sufficient to enable cost-effective identification of commercial-scale product volumes. The number of available spectral signature combinations range from identifying product manufacturer or brand, to product type or model, to individual lot or batch numbers across multiple industries and markets.

In some embodiments, the unique optical signature of each tag can be read using an absolute or a relative spectral measurement device, apparatus, or system. In some embodiments, tags comprise the surface of a silicon wafer that is etched to have a spectral code encoded by the etching. A thin layer from the surface of the etched wafer is removed and divided into small tags, and the resultant tags contain a complex porous nanostructure that is programmed during electrochemical synthesis to display a unique reflectivity spectrum. The tags are then oxidized by a high-temperature bake step to turn the crystalline, nanoporous silicon tags into amorphous, nanoporous silica. This bake step stabilizes the nanoporous structure against further oxidation (thus stabilizing the spectral signature) and provides for the tags to be characterized as a GRAS excipient.

In some embodiments, the spectrum of one or more tags is measured in an absolute or relative spectral measurement system, then verified against other information as part of a database or located on a label or package. In some embodiments, the tags are used on their own acting simply as labels for quality assurance or other purposes. Information capacity is based on the number of possible unique spectra, using different peak numbers, peak placements, peak rugate phases, and/or peak amplitudes as modulation parameters. The tags are passive, inconspicuous and can be attached to the outside of medicines or food products to be read, for example, through clear or translucent plastic blister packs, or mixed into medicines or food as a forensic excipient, to be read as part of an investigation or inspection process by authorized security or quality assurance personnel.

In various embodiments, the tag properties comprise one or more of the following:

- Inconspicuous size range (≈50 to 100 micrometers) allows covert or semi-covert use
- Edible and biologically inert
- High temperature resistance—melting point above 1000° C.
- Passive—no energy input or output
- Are used in or on a product, package, label, or security fiber
- Are applied via sprays, coatings, varnishes, or as part of laminate
- Are integrated at a number of manufacturing stages
- High level of security possible; can be scaled to suit specific product needs
- Are made so as to be self-authenticating and thereby have a reduced cost and security risk as compared to systems with online databases and maintenance In some embodiments, the optical measurement system includes a lens for collecting light from the sample with a good working distance and field of view (e.g., ~10 mm diameter field of view, 2× objective lens with numeric aperture (NA) of ~0.05-0.07, and working distance of ~3-7 mm). In some embodiments, the objective lens will be operated in a telecentric arrangement to ensure that the system captures tilted tags.

In some embodiments, the system comprises a sample holder for holding a sample (e.g., a sample that includes a tag). The sample holder comprises a sample input port for allowing system operator to place the sample into the sample holder. The sample holder is placed anywhere within an initial area in the sample holder. The sample holder additionally comprises a bottom (e.g., a bottom for supporting the sample—for example, preventing the sample from falling through the sample holder). The sample holder additionally comprises an actuator for actuating the sample holder. In some embodiments, the actuator comprises a manual actuator (e.g., an actuator that mechanically causes parts to move under a manual force)—for example, a lever, a twist ring, a pull string, etc. The actuator actuates one or more moving parts within the sample holder. In some embodiments, the actuator actuates one or more arms. The one or more arms comprise arms for moving a sample from an initial location in the initial area to a target area. In some embodiments, the target area is small (e.g., a predetermined position with some small amount of acceptable variability). In some embodiments, the one or more arms additionally comprise arms for holding a sample (e.g., for preventing the sample from moving in the x-axis, the y-axis, or the z-axis). In some embodiments, the one or more arms additionally comprise arms for holding a sample within the target area. In some embodiments, the actuator actuates one or more bottom actuators. The one or more bottom actuators comprise bottom actuators for moving the bottom to provide optical access to the sample (e.g., under the target area). In some embodiments, the one or more bottom actuators comprise an aperture. In some embodiments, the sample does not fall through the optical access to the bottom after actuation of the bottom actuators because the sample is held by the one or more arms. In some embodiments, the actuator first actuates the one or more arms to move the sample to the target area and hold the sample, and then actuates the bottom actuators to provide optical access to the sample.

In some embodiments, the sample holder has the ability to place a sample "roughly" in x, y, with z specified by a floor. The sample holder arms sweep a sample by covering all of x, y (e.g., an initial area or well of the sample holder). The arms center a sample to 0,0 or the origin (e.g., a target area of the sample holder) without regard to the initial sample orientation. The sample holder then retracts the floor for an unobstructed view of the sample. There is no glass floor in the way. The sample holder performs the sweeping of the arms and the retraction of the floor in sequence through a simple motion (e.g., a twist of the large outer ring of the sample holder). Further, the reverse procedure, reinsertion of the floor followed by retraction of the arms, is performed by the simple motion reversed.

In various embodiments, the sample holder is used to hold a sample for a laser etching tool, ink-jet printing, marking individual pills with a marking such as a serial number, or any other appropriate operation on a sample that is held. These embodiments also rely on the unobstructed (glass free) holding of the sample.

Figure 2:
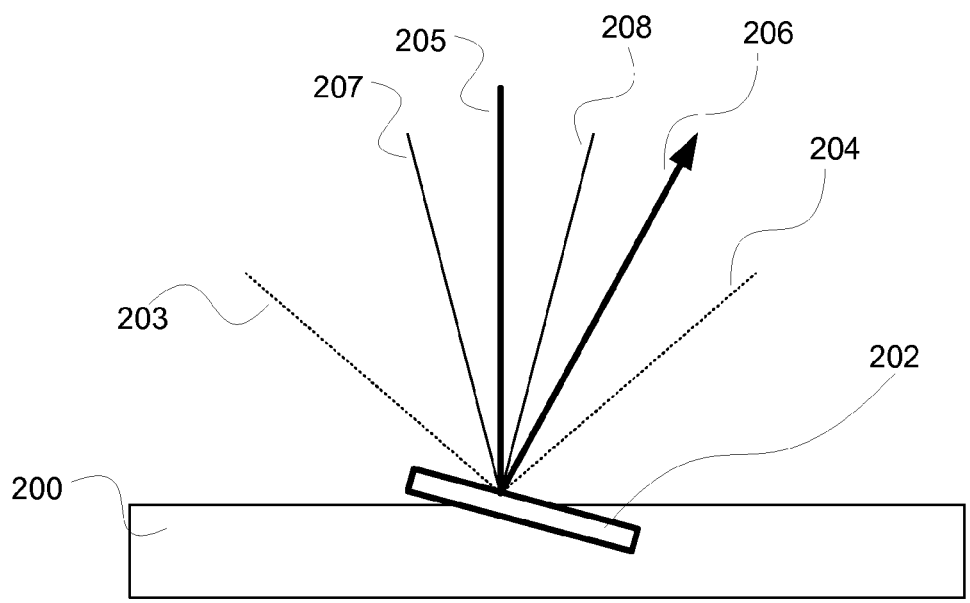
FIG. 2 is a diagram illustrating an embodiment of tag measurement geometry.

FIG. 1 is an image illustrating an embodiment of a tag. In the example shown, tag 100 is a 50 um to 100 um sized irregularly shaped tag. The tags are 20 um thick. These tags are imaged using an Ocean Optics USB2000+ spectrometer with broadband illumination from a halogen source FIG. 2 is a diagram illustrating an embodiment of tag measurement geometry. In the example shown, tag 202 is partially embedded in substrate 200 (e.g., at an angle to the surface of the substrate). Illumination beam (e.g., beam 205) is incident within angular cone outlined by 207 and 208. Collection aperture is different from illumination beam and is outlined with 203 and 204. In this case, the larger collection aperture as compared to the illumination beam enables the collection of reflected light from tilted tags. In some embodiments, beam 206 is reflected beam from incident beam 205.

Figure 3:
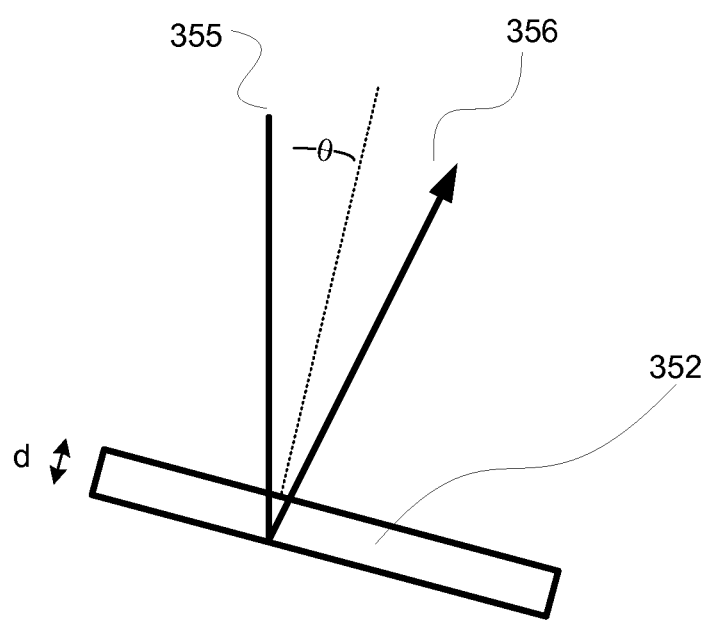
FIG. 3 is a diagram illustrating an embodiment of spectral dependence associated with geometry.

FIG. 3 is a diagram illustrating an embodiment of spectral dependence associated with geometry. In the example shown, tag 352 surface normal is angle θ with respect to incident light 355. A reflected spectral peak location is a function of the optical path length of the beam within the tag. The path is a function of the angle between the light ray and the surface of the tag and is proportional to $d/\cos(\theta)$. Thus, the spectrum from a tilted tag is shifted. In addition, the peaks broaden and become lower (perhaps due to scattering within the tag). In some embodiments, beam 356 is reflected beam from incident beam 355.

In some embodiments, the reflections of multiple tags at different angles will broaden the reflection peaks. In some embodiments, variations in tags also will broaden the reflection peaks.

Figure 4:
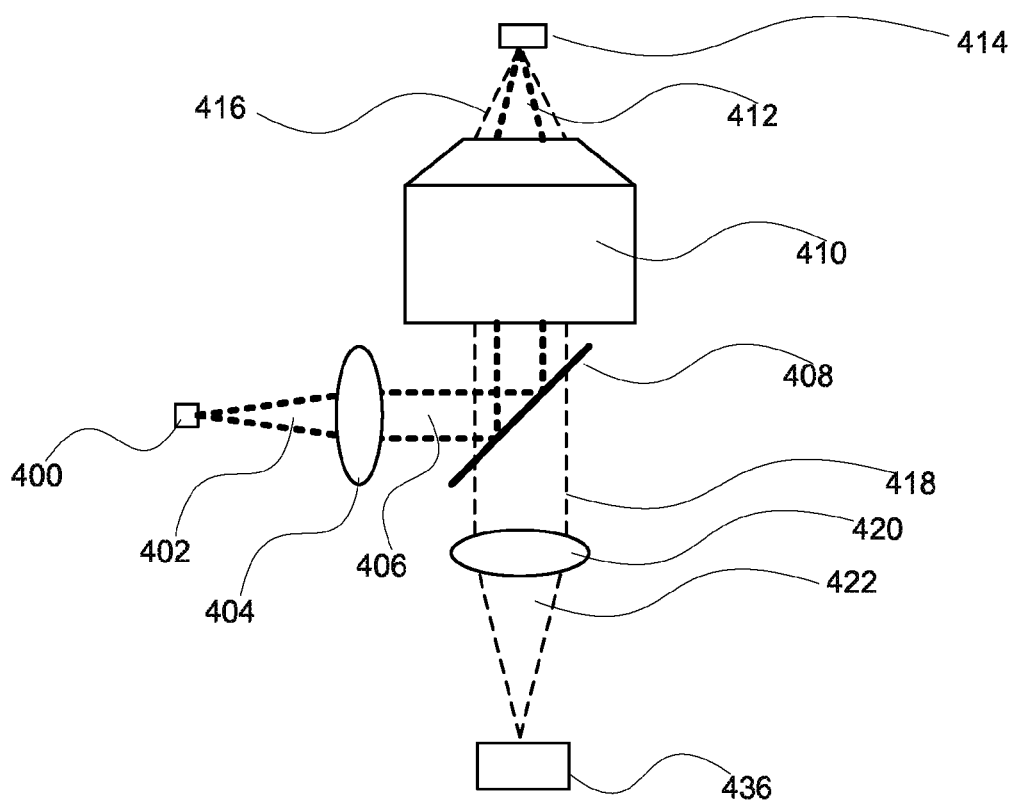
FIG. 4 is a diagram illustrating an embodiment of a system for optical measurement.

In some embodiments, the tags are specular reflectors and not diffuse reflectors. Therefore, the tags can either be illuminated at a large angle orthogonal to the object surface, or the tags can be combined using a diffuser and lens to form a combined multispectral high NA beam orthogonal to the surface FIG. 4 is a diagram illustrating an embodiment of a system for optical measurement. In the example shown, source 400 provides broadband illumination to sample 414. For example, source 400 comprises a white light emitting diode, a tungsten source, an incandescent source, or any other appropriate source. Light from source 400 propagates along path 402 and is collimated using lens 404. Light propagates along path 406 and at least a portion is reflected by beam splitter 408 through objective 410, travels on path 412, and is focused on sample 414. Reflected light from sample 414 propagates along path 416. Numerical aperture of incident beam is different from the numerical aperture of the reflected beam (e.g., NA of incident beam is smaller than NA of reflected beam).

In the example shown, reflected light from sample is collimated and propagates along 418 with at least a portion of the beam transmitting through beam splitter 408. The reflected light is focused using lens 420 to focus on detector 436.

Figure 5:
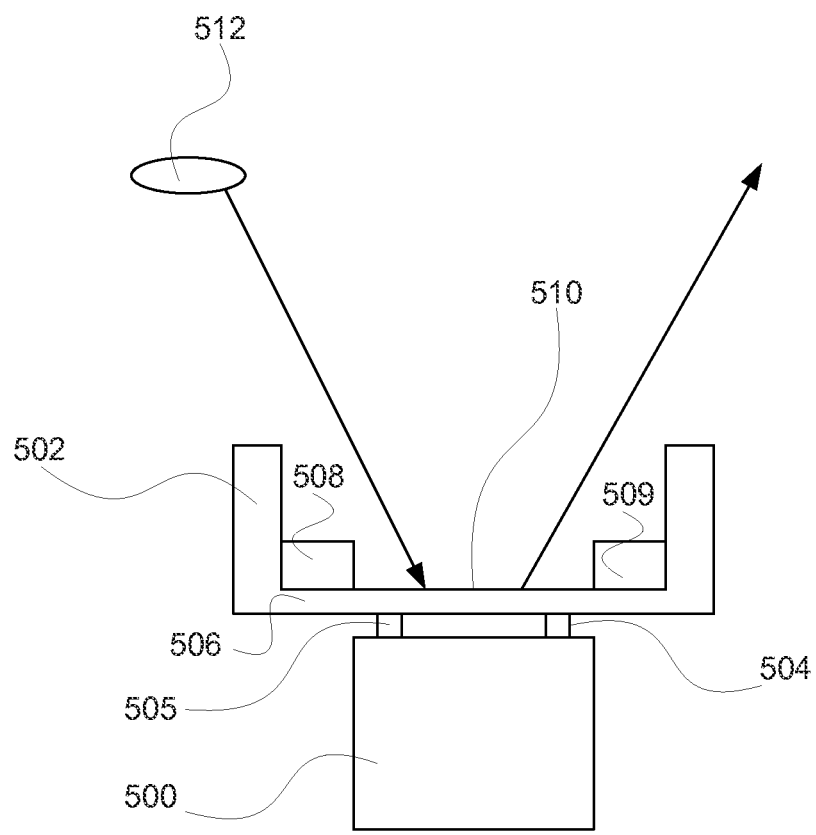
FIG. 5 is a diagram illustrating an embodiment of a system for optical measurement with a sample holder.

FIG. 5 is a diagram illustrating an embodiment of a system for optical measurement with a sample holder. In some embodiments, optical measurement system 500 comprises optical measurement system of FIG. 4. In the example shown, the system includes sample holder 502. The sample holder 502 holds a sample (e.g., sample 512) for measurement by system for optical measurement system 500. In some embodiments, sample holder 502 holds the sample in a predetermined position for measurement by system for optical measurement system 500. Sample holder 502 is aligned to system for optical measurement system 500 using alignment posts (e.g., alignment post 804, alignment post 505, etc.). In various embodiments, sample holder 502 is aligned to system for optical measurement system 500 using 1, 2, 3, 4, 5, or any other appropriate number of alignment posts. In various embodiments, alignment posts comprise magnetically orienting posts, nesting posts, meshing teeth, or any other appropriate alignment devices. Sample holder 502 additionally comprises bottom 506. In some embodiments, bottom 506 comprises a bottom for holding a sample. In some embodiments, bottom 506 comprises an initial area (e.g., an area where it is possible for an operator to initially place a sample). In some embodiments, bottom 506 comprises one or more bottom actuators for moving the bottom to provide optical access to the sample. Sample holder 502 comprises one or more arms (e.g., arm 508, arm 509, etc.). In some embodiments, the one or more arms actuate to move a sample in the initial area to a target area (e.g., target area 510), wherein the one or more arms hold the sample. In some embodiments, target area 510 comprises the optimal location for optical measurement by system for optical measurement system 500. In some embodiments, sample 512 is placed in the initial area (e.g., by an operator), moved to target area 510 and held by the one or more arms, optical access is provided to sample 512 by the motion of the one or more bottom actuators, sample 512 is measured (e.g., optically) by system for optical measurement system 500, optical access to sample 512 is closed (e.g., by a reverse motion of the one or more bottom actuators), the one or more arms release sample 512, and sample 512 is removed (e.g., by the operator).

Figure 6:
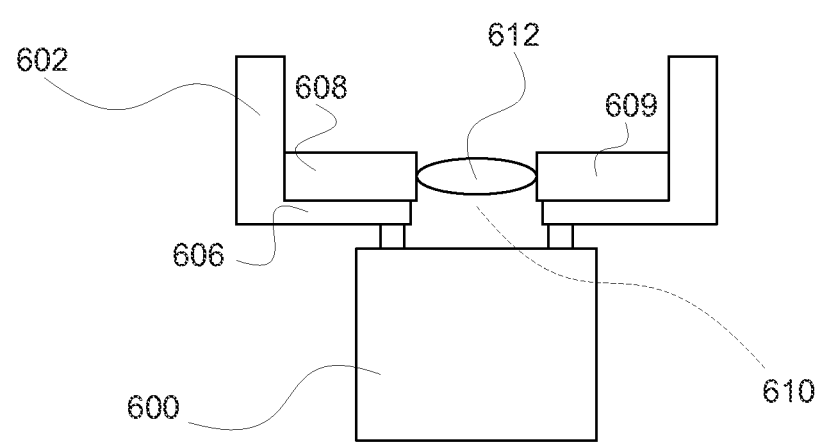
FIG. 6 is a diagram illustrating an embodiment of a system for optical measurement with a sample holder holding a sample.

FIG. 6 is a diagram illustrating an embodiment of a system for optical measurement with a sample holder holding a sample. In some embodiments, the system for optical measurement of FIG. 6 comprises the system for optical measurement of FIG. 5 holding a sample. In the example shown, sample holder 602 comprises fixed bottom 602 (e.g., a portion of the bottom of sample holder 602 that does not move) and aperture 610 (e.g., a region when actuators have moved a portion of the bottom of sample holder 606 to create an aperture). Sample holder 600 additionally comprises one or more arms (e.g., arm 608, arm 609, etc.) that have been actuated to move sample 612 into position for measurement (e.g., over aperture 610) and hold sample 612 such that it does not fall when aperture 610 opens.

Figure 7:
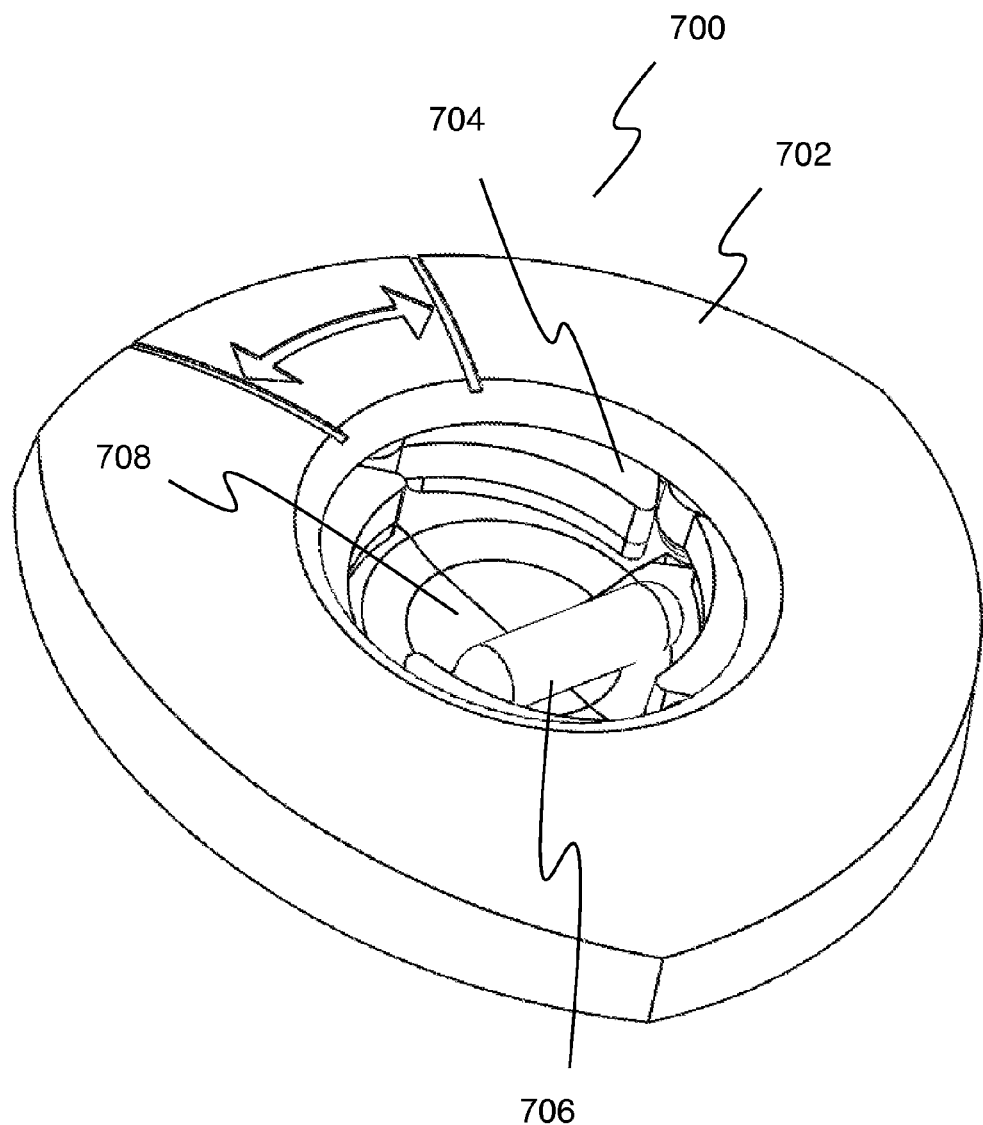
FIG. 7 is a diagram illustrating an embodiment of a sample holder.

FIG. 7 is a diagram illustrating an embodiment of a sample holder. In some embodiments, sample holder 700 of FIG. 7 comprises sample holder 502 of FIG. 5. In the example shown, sample holder 700 comprises cover 702. In some embodiments, cover 702 comprises a sample holder cover for protecting the moving parts of sample holder 700. In some embodiments, cover 702 comprises a handle mounted to an actuator (e.g., a rotational actuator). Sample 706 comprises a sample placed within sample holder 700. In some embodiments, sample 706 comprises a pill. In some embodiments, sample 706 comprises a pill including a coating. In various embodiments, the shape of sample 706 is round, elliptical, oval, oblong, or any other appropriate shape. In some embodiments, when sample holder 706 is placed within sample holder 700, it is placed within an initial area (e.g., an area acceptable for placing the sample, e.g., an area large enough to place and retrieve the sample by hand). In some embodiments, the initial area comprises all of the area where sample 706 can be initially placed within sample holder 700. In some embodiments, the initial area comprises an initial area for supporting a sample (e.g., for preventing the sample from falling through the sample holder—for example, holding the sample in the z direction). In some embodiments, rotating cover 702 (e.g., relative to the rest of sample holder 700) actuates one or more arms (e.g., arm 704). In some embodiments, actuating one or more arms causes sample 706 to be moved to a target area. In some embodiments, actuating one or more arms causes sample 706 to be held by the one or more arms. In some embodiments, rotating cover 702 actuates one or more bottom actuators, causing one or more bottom sections (e.g., bottom section 708) to move to create an aperture. In some embodiments, the aperture is directly beneath the target area.

Figure 8:
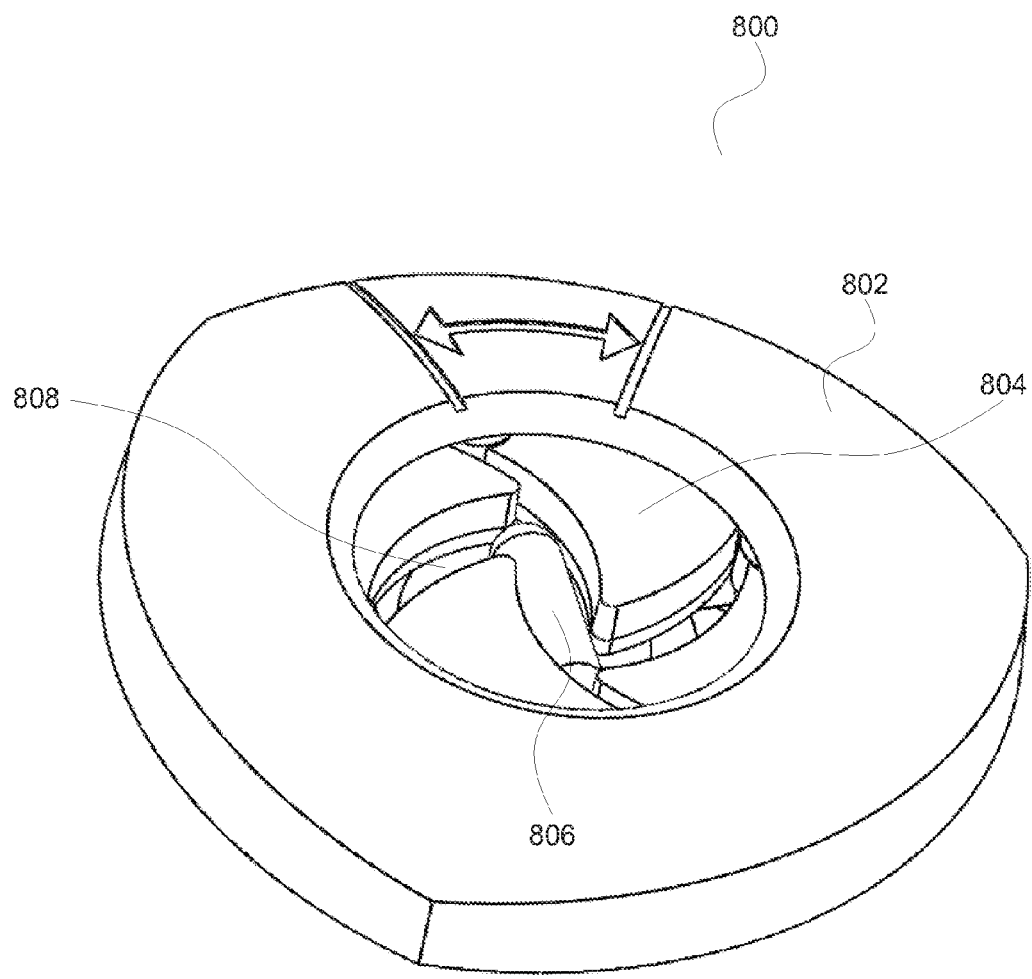
FIG. 8 is a diagram illustrating an embodiment of a sample holder.

FIG. 8 is a diagram illustrating an embodiment of a sample holder. In some embodiments, sample holder 800 of FIG. 8 comprises sample holder 502 of FIG. 5. In the example shown, sample holder 800 comprises cover 802. In some embodiments, cover 802 comprises a sample holder cover for protecting the moving parts of sample holder 800. In some embodiments, cover 802 comprises a handle mounted to an actuator (e.g., a rotational actuator). Sample 806 comprises a sample placed within sample holder 800. In some embodiments, sample 806 comprises a pill. In some embodiments, sample 806 comprises a pill including a coating. In various embodiments, the shape of sample 806 is round, elliptical, oval, oblong, or any other appropriate shape. In some embodiments, when sample holder 806 is placed within sample holder 800, it is placed within an initial area (e.g., an area acceptable for placing the sample, e.g., an area large enough to place and retrieve the sample by hand). In some embodiments, the initial area comprises all of the area where sample 806 can be initially placed within sample holder 800. In some embodiments, the initial area comprises an initial area for supporting a sample (e.g., for preventing the sample from falling through the sample holder—for example, holding the sample in the z direction). In some embodiments, rotating cover 802 (e.g., relative to the rest of sample holder 800) actuates one or more arms (e.g., arm 804). In the example shown, sample holder 800 is holding a sample after the actuating of the one or more arms and this has caused sample 806 to be moved to a target area. In some embodiments, actuating one or more arms causes sample 806 to be held by the one or more arms. In some embodiments, rotating cover 802 actuates one or more bottom actuators, causing one or more bottom sections (e.g., bottom section 808) to move to create an aperture. In some embodiments, the aperture is directly beneath the target area.

Figure 9:
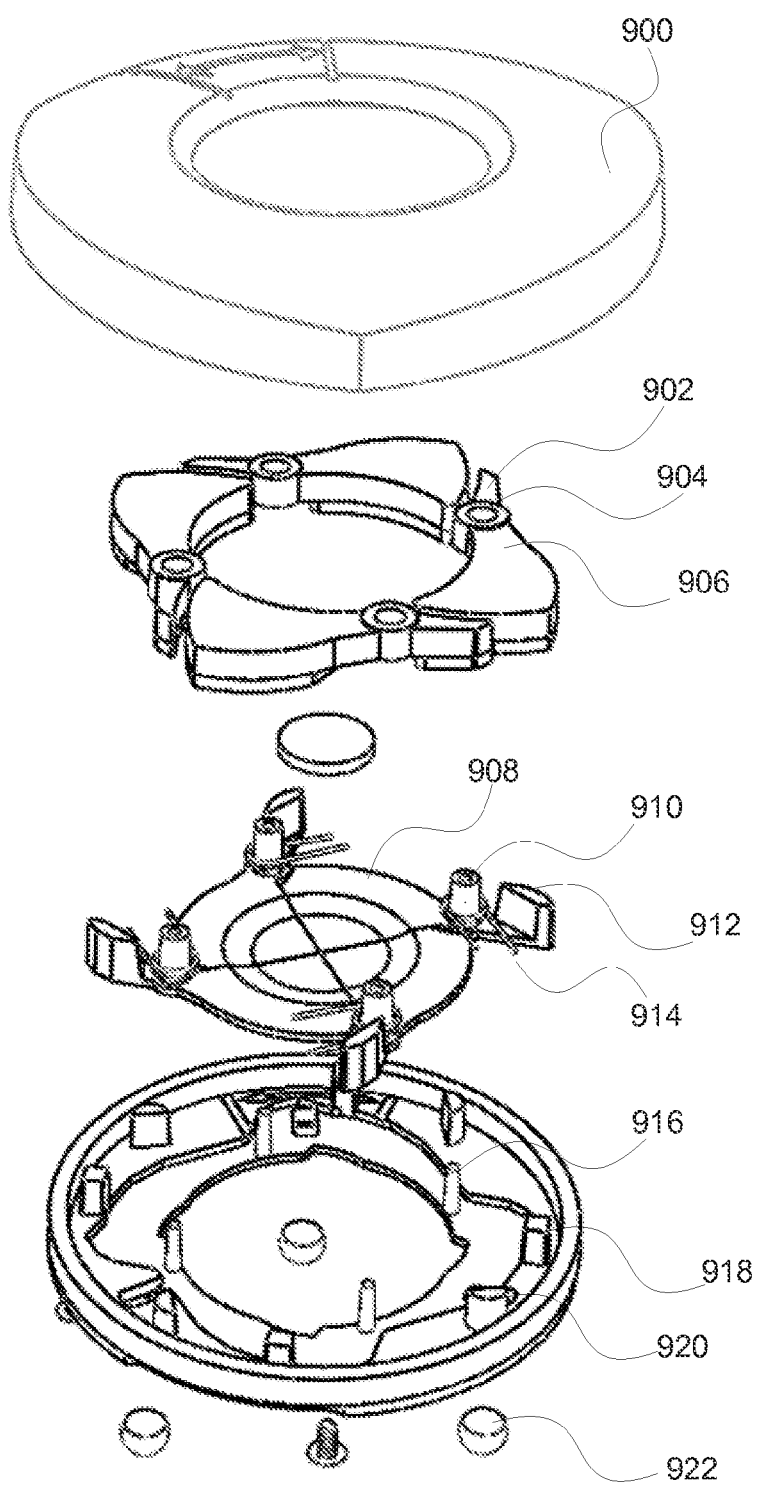
FIG. 9 is a diagram illustrating an embodiment of a sample holder.

FIG. 9 is a diagram illustrating an embodiment of a sample holder. In some embodiments, the sample holder of FIG. 9 is an exploded view of sample holder 700 of FIG. 7 or sample holder 800 of FIG. 8. In the example shown, cover 900 rotates to actuate arms. For example, features articulated on the bottom of cover 900 release arms to sweep a sample in an initial area and hold the sample at a target area. Each arm pivots about a pivot (e.g., pivot 904) with a sweep/hold portion of the arm (e.g., arm portion 906) and an opening lever (e.g., opening lever 902). Cover 900 after releasing arms so that the sample is held, can rotate farther to actuate bottom arms (e.g., bottom arm 908) to enable access to sample for an optical measurement system beneath the sample holder. The bottom arms pivot about a pivot (e.g., pivot 910) and are actuated when an opening lever (e.g., lever 912) is engaged by articulated features on the bottom of cover 900. In some embodiments, the articulated features used to actuate the sweeping/holding arms are the same features as are used to actuate the opening of the bottom arms. Springs (e.g., spring 914) are used to close each arm individually to grab a sample in the sample holder. Bottom of sample holder includes pivot axes (e.g., pivot axis 916) as well as open stops (e.g., stop 920) and close stops (e.g., stop 918). Bottom of sample holder also has mounting features (e.g., metal ball 922 that enable the use of a magnetic mounting to an optical measurement system).

In some embodiments, the sweeping/holding arms for the sample pivot around the same pivot axis as the bottom arms that open the aperture for optical measurement (e.g., pivot 904, pivot 910, and pivot axis 916).

Figure 10:
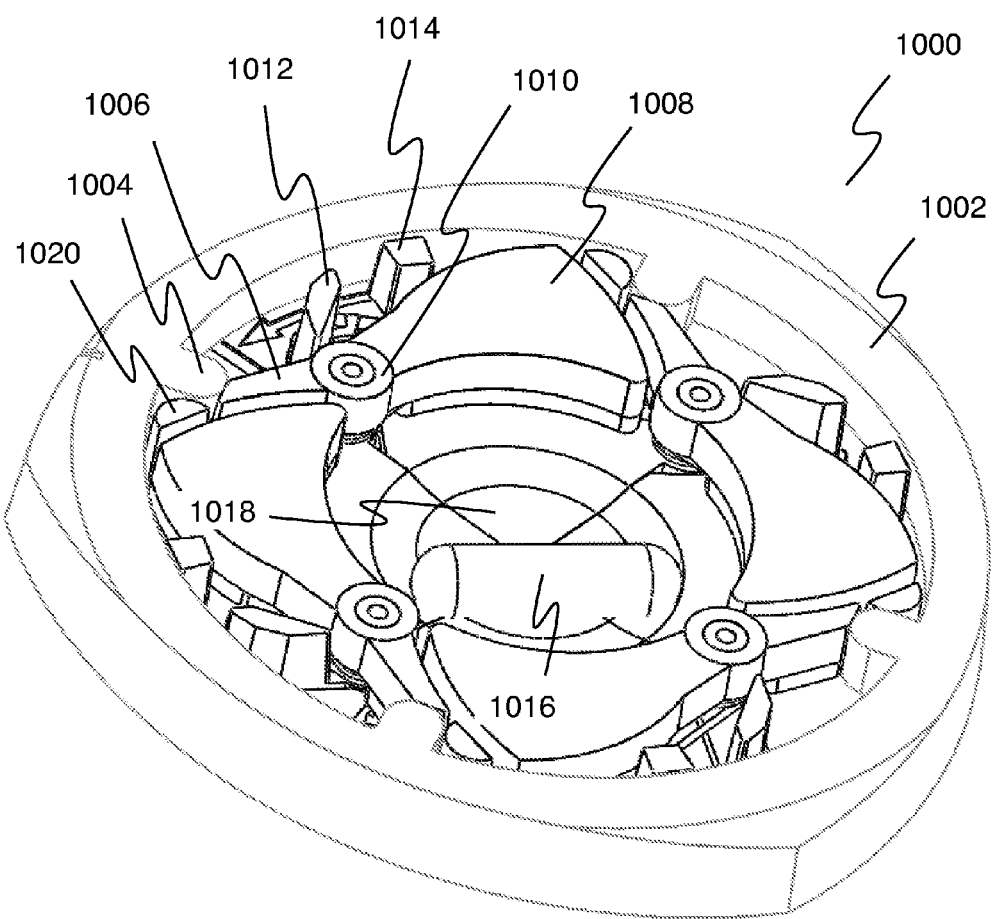
FIG. 10 is a diagram illustrating an embodiment of a sample holder.

FIG. 10 is a diagram illustrating an embodiment of a sample holder. In some embodiments, sample holder 1000 comprises sample holder 900 of FIG. 9 with the cover (e.g., cover 902) not shown. In the example shown, sample holder 1000 comprises actuation ring 1002. Actuating sample holder 1000 comprises turning actuation ring 1002. In some embodiments, actuating sample holder 1000 comprises turning actuation ring 1002 clockwise. Actuation ring 1002 is shown in the default (e.g., non-actuated) position. In some embodiments, actuating sample holder 1000 comprises actuating one or more arms (e.g., arm 1008). In some embodiments, actuating sample holder 1000 comprises actuating one or more bottom actuators (e.g., bottom arm 1018). In some embodiments, actuation ring 1002 is connected to a cover. Actuation ring 1002 includes cam 1004 (e.g., an articulated feature that engages arms to actuate the arms). In the default position (e.g., against open stop 1020), cam 1004 holds lever 1006 pushed towards the center of sample holder 1000. Lever 1006 comprises part of arm 1008, and lever 1006 and arm 1008 rotate about post 1010 (e.g., when lever 1006 is positioned towards the center of sample holder 1000, arm 1008 is positioned away from the center of sample holder 1000; and when lever 1006 is positioned away from the center of sample holder 1000, arm 1008 is positioned towards the center of sample holder 1000). In some embodiments, arm 1008 comprises a spring (e.g., a torsion spring—for example, mounted around post 1010) for pushing lever 1006 and arm 1008. In some embodiments, the spring pushes lever 1006 and arm 1008 towards a position where arm 1008 is towards the center of sample holder 1000 and lever 1006 is away from the center of sample holder 1000. In the default position, cam 1004 holds the spring in tension. When actuation ring 1002 is actuated (e.g., turned clockwise), cam 1004 no longer holds lever 1006 pushed towards the center of sample holder 1000, and the spring pulls lever 1006 away from the center of sample holder 1000 and arm 1008 towards the center of sample holder 1000. Each arm is independently pushed by a spring mounted around a pivot of the arm. In some embodiments, sample holder 1000 comprises four arms (e.g., arm 1008) that each move in a similar fashion as actuation ring 1002 is actuated. In various embodiments, sample holder 1000 comprises 1, 2, 3, 4, 5, 6, 8, 12, 14, 17 or any other appropriate number of arms. In some embodiments, three arms are selected for the sample holder because it is suitable for round objects. In some embodiments, four arms are selected for the sample holder because it is suitable for round objects and has dual symmetry more suitable for oblong objects.

In some embodiments, when the arms of sample holder 1000 move towards the center of sample holder 1000, a sample within an initial area of sample holder 1000 (e.g., sample 1016) is swept to a target area. In some embodiments, after the sample is swept to the target area, it is held by the arms. In some embodiments, holding the sample comprises not allowing the sample to move in the x-y plane (e.g., in the plane of the arms). In some embodiments, holding the sample comprises not allowing the sample to move in the z plane (e.g., perpendicular to the plane of the arms, e.g., up and down). In some embodiments, the target area comprises an area where the sample is optically measured. As actuation ring 1002 is actuated (e.g., past fully releasing lever 1006), cam 1004 pushes bottom actuator 1012. In some embodiments, cam 1004 pushing bottom actuator 1012 comprises actuating bottom actuator 1012. In some embodiments, bottom actuator 1012 comprises part of a bottom section (e.g., bottom arm 1018) that pivots about the same post 1010. In some embodiments, cam 1004 pushing bottom actuator 1012 towards the center of sample holder 1000 moves the bottom section so that it opens an aperture at the bottom of the sample holder. Cam 1004 can rotate until stopped by hold stop 1014, where the sample holder is holding a sample with arms moved to the center and the bottom sections moved away from the center. In the example shown, sample holder 1000 comprises four bottom actuators (e.g., bottom actuator 1012). In various embodiments, sample holder 1000 comprises 1, 2, 3, 4, 5, 6, 8, 11, 12, 13, 17 or any other appropriate number of bottom actuators. In some embodiments, the one or more bottom actuators move the bottom to provide optical access to the sample. In some embodiments, the bottom no longer supports the sample when optical access is provided to the sample. In some embodiments, sample holder 1000 comprises the same number of arms and bottom actuators. In some embodiments, sample holder 1000 comprises different numbers of arms and bottom actuators. When bottom actuator 1012 is pushed by cam 1004 and the associated bottom section is moved, an aperture in the bottom of sample holder 1000 is formed. In some embodiments, the aperture is formed beneath the target area. In some embodiments, sample holder 1000 comprises no moving parts for creating an aperture (e.g., no bottom actuators and no bottom sections) and instead comprises a bottom section transparent to light (e.g., a glass bottom section, a quartz bottom section, etc.).

Figure 11:
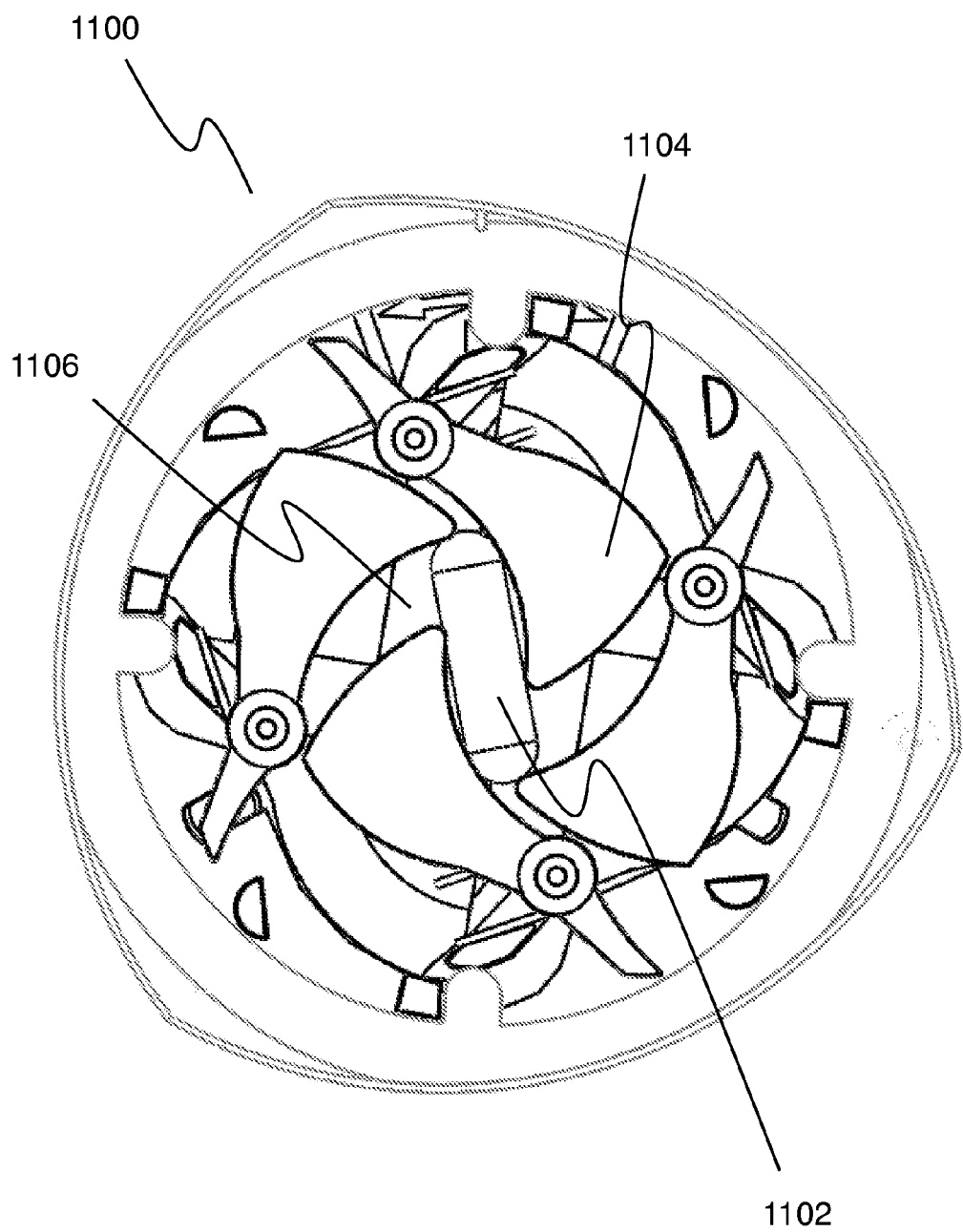
FIG. 11 is a diagram illustrating an embodiment of a sample holder.

FIG. 11 is a diagram illustrating an embodiment of a sample holder. In some embodiments, sample holder 1100 comprises sample holder 1000 of FIG. 10. In the example shown, sample holder 1100 is shown in the actuated position. Sample holder 1100 comprises a set of arms (e.g., arm 1104) holding sample 1102 over aperture 1106. In some embodiments, each arm of the set of arms is individually spring turned to sweep the initial open area to move and hold a sample (e.g., sample 1102) at a target location over aperture 1106.

Figure 12:
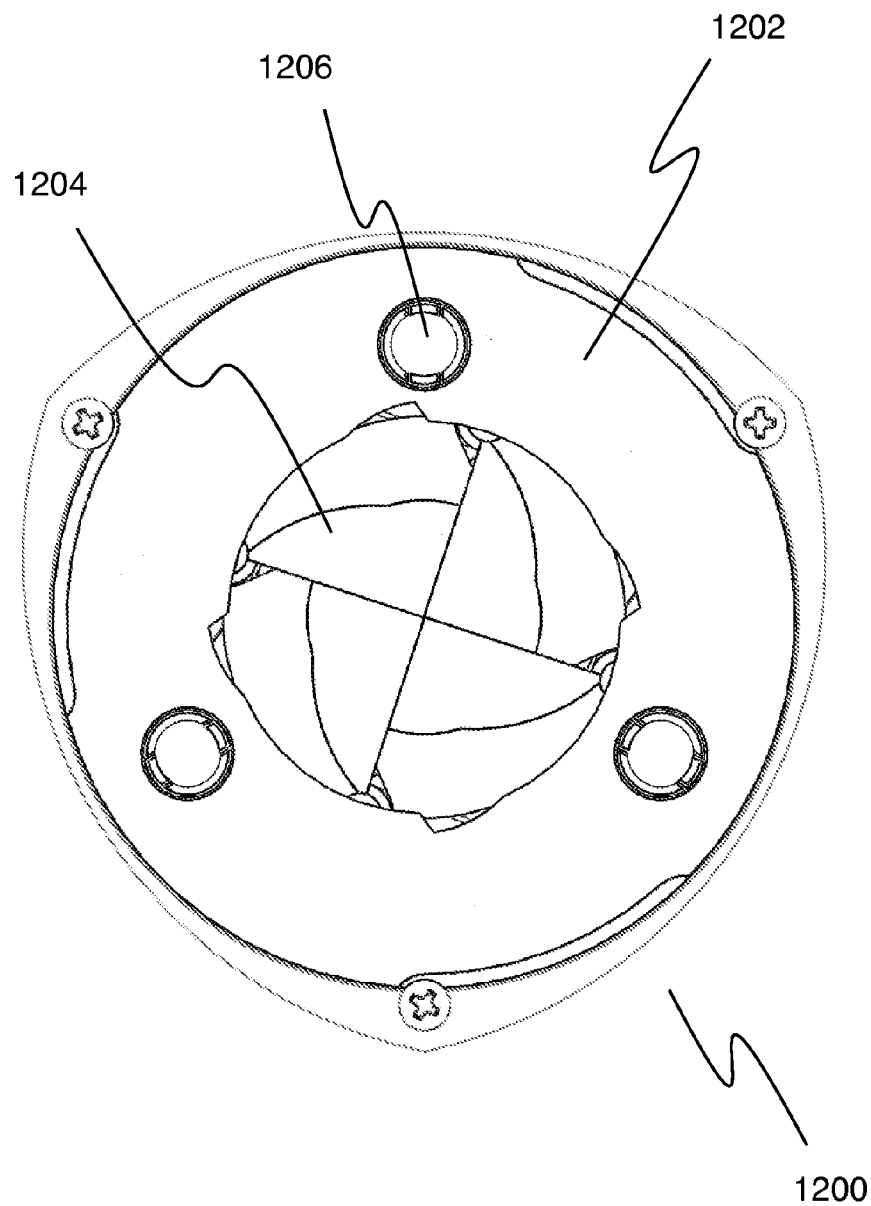
FIG. 12 is a diagram illustrating an embodiment of a sample holder.

FIG. 12 is a diagram illustrating an embodiment of a sample holder. In some embodiments, sample holder 1200 comprises sample holder 1000 of FIG. 10. In the example shown, sample holder 1200 is shown from a bottom view (e.g., the bottom of sample holder 1200 is shown). Sample holder 1200 is shown in a default (e.g., non-actuated) position. Sample holder 1200 comprises static bottom 1202 and a set of moving bottom sections (e.g., bottom section 1204). Sample holder 1200 comprises four moving bottom sections. Static bottom 1202 comprises an aperture. When sample holder 1200 is actuated, each moving bottom section of the set of moving bottom sections moves to leave an aperture in the bottom of sample holder 1202. When sample holder 1200 is actuated, a sample is held over the region of the aperture. Sample holder 1200 comprises a set of alignment posts (e.g., alignment post 1206) for alignment. In some embodiments, the set of alignment posts comprises one or more magnetic aligners. In some embodiments, the set of alignment posts aligns sample holder 1200 to an external system (e.g., an optical measurement system—for example, a sample reader). In various embodiments, sample holder 1200 comprises 1, 2, 3, 4, 5, 8, 11, 14, or any other appropriate number of alignment posts. In some embodiments, there are three posts and the three posts comprise balls, where each ball engages a "V block" (not shown) on the instrument. The ball/V block is a traditional kinematic mount ensuring repeatable placement on the instrument.

Figure 13:
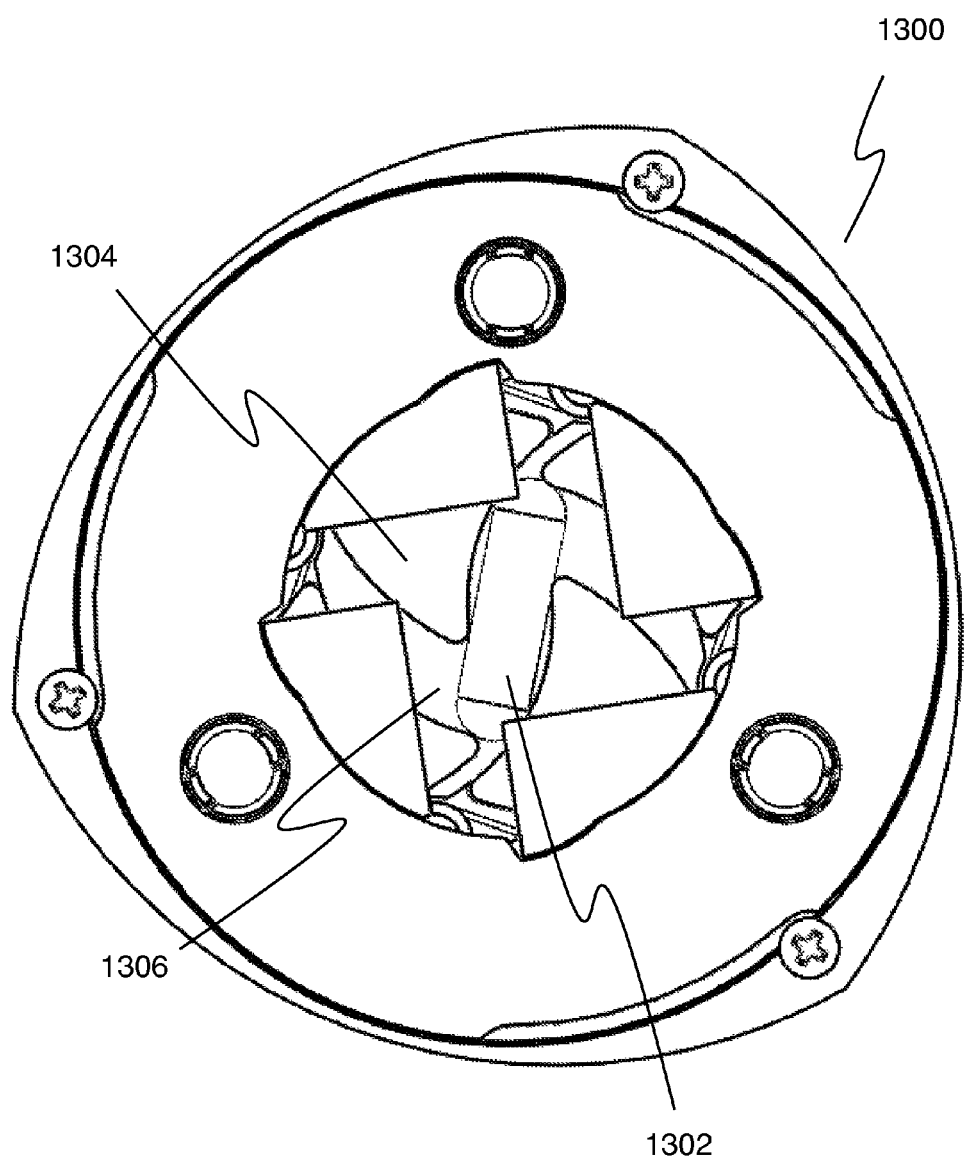
FIG. 13 is a diagram illustrating an embodiment of a sample holder.

FIG. 13 is a diagram illustrating an embodiment of a sample holder. In some embodiments, sample holder 1300 comprises sample holder 1200 of FIG. 12 shown in the actuated position. In the example shown, sample holder 1300 is shown from a bottom view. Sample holder 1300 comprises a set of arms (e.g., arm 1304) holding sample 1302 over aperture 1306. The aperture is created as the bottom is actuated away from sample 1302.

Figure 14:
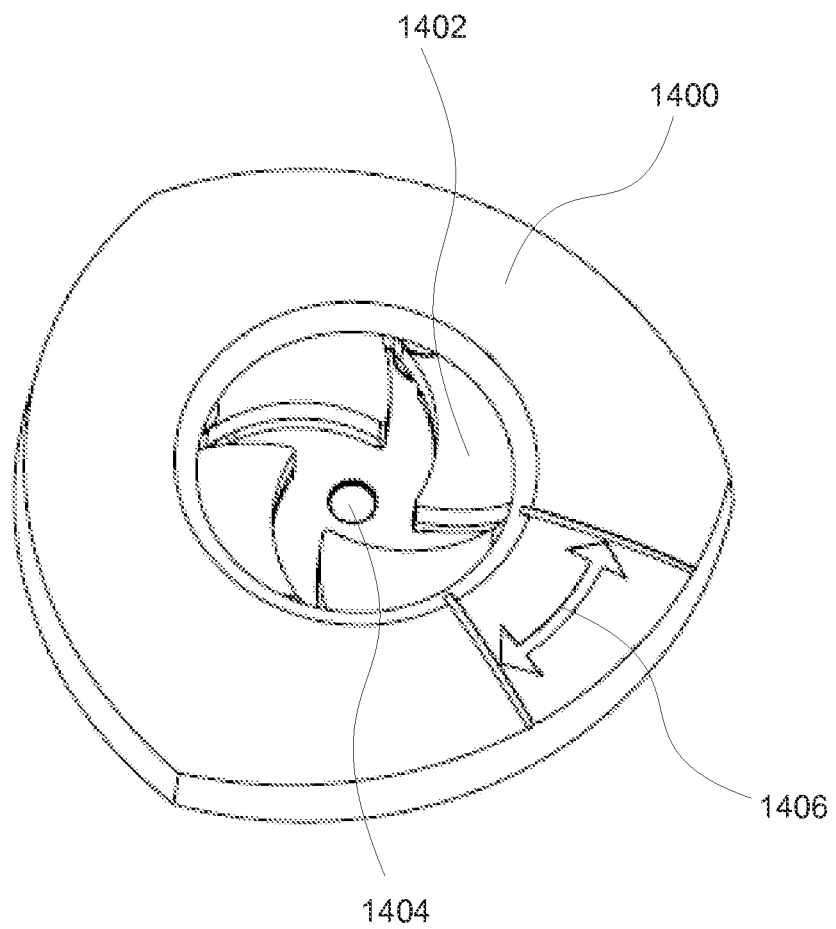
FIG. 14 is a diagram illustrating an embodiment of a sample holder with a bottom aperture.

FIG. 14 is a diagram illustrating an embodiment of a sample holder with a bottom aperture. In the example shown, sample holder 1400 is actuated by rotation of the top either clockwise or counterclockwise (e.g., in the direction of arrow 1406). The actuation causes arms (e.g., arm 1402) to sweep a sample in the initial area (e.g., the area when the arms are retracted) to a target area (e.g., over aperture 1404). The arms sweep until the sample is held (e.g., not able to move) for optical measurement via aperture 1404. In various embodiments, aperture 1404 is an aperture integral to the bottom of sample holder 1400, is a removable aperture (e.g., so that different aperture sizes can be placed at the bottom of the sample holder), is smaller than sample (e.g., so that the edges of the aperture prevent the sample from falling through the aperture but so that an optical measurement can be made through the aperture of the sample), or any other appropriate aperture.

Figure 15:
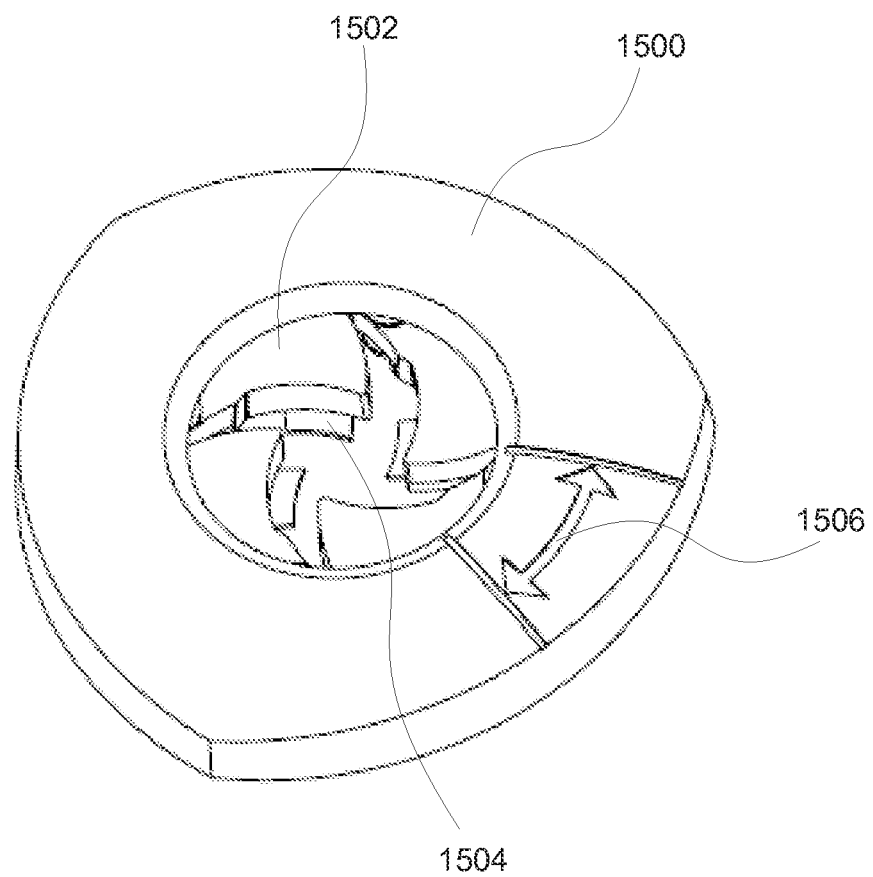
FIG. 15 is a diagram illustrating an embodiment of a sample holder with a bottom aperture.

FIG. 15 is a diagram illustrating an embodiment of a sample holder with a bottom aperture. In the example shown, sample holder 1500 is actuated by rotation of the top either clockwise or counterclockwise (e.g., in the direction of arrow 1506). The actuation causes arms (e.g., arm 1502) to sweep a sample in the initial area (e.g., the area when the arms are retracted) to a target area. The arms sweep until the sample is held (e.g., not able to move) for optical measurement via an aperture or bottom that moves away (not shown). The arms have ledges (e.g., ledge 1504) that prevent the sample from falling. In various embodiments, ledge 1504 is integral to the bottom of an arm, is a removable (e.g., so that different ledge sizes can be placed at the bottom of the arm for different sample geometries), is fixed, is actuated to protrude as the arm sweeps the sample to the target area, or any other appropriate ledge.

Figure 16:
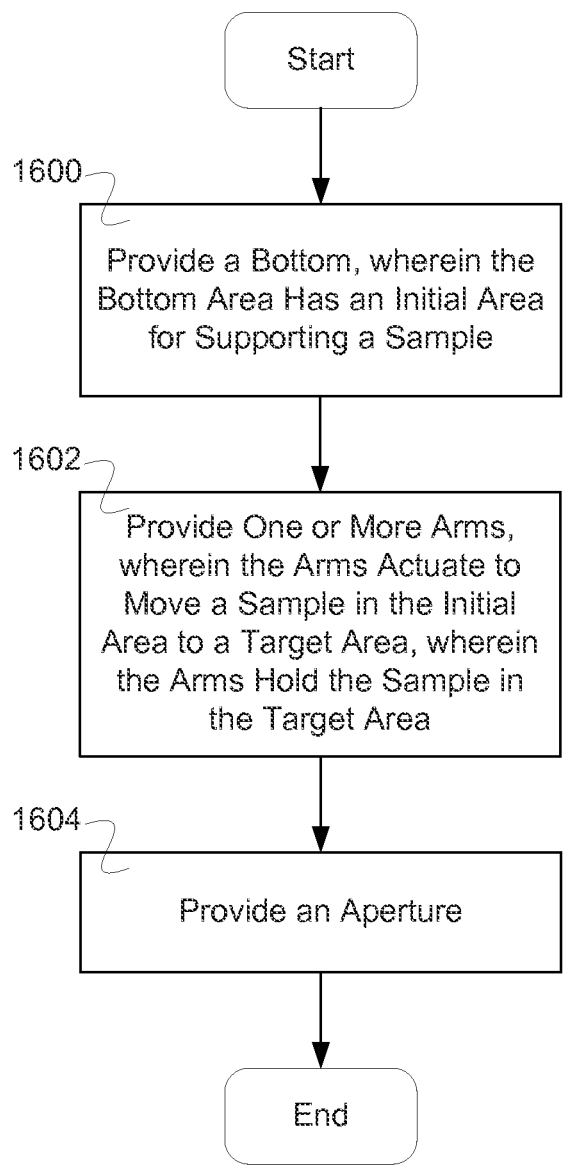
FIG. 16 is a flow diagram illustrating an embodiment of a process for a sample holder.

FIG. 16 is a flow diagram illustrating an embodiment of a process for a sample holder. In the example shown, in 1600 a bottom is provided, wherein the bottom has an initial area for supporting a sample. For example, an initial area is provided for a sample to be placed into, where the bottom supports the sample. In some embodiments, the initial area is bounded on the sides by the surfaces of one or more arms. In 1602, one or more arms are provided, wherein the one or more arms actuate to move the sample in the initial area to a target area, wherein the one or more arms hold the sample in the target area (e.g., after having been moved from the initial area to the target area). For example, the actuation of the sample holder comprises rotating a top of the sample holder, and the one or more arms move to sweep the initial area so as to move the sample in the initial area to a target area. In 1604, an aperture is provided. In various embodiments, an aperture is opened (e.g., by moving bottom plates to create an aperture), an aperture exists in the bottom of the sample holder at the target area (e.g., a hole exists smaller than the sample but large enough to allow an optical measurement to be made through), or any other appropriate aperture. In some embodiments, the aperture comprises a transparent bottom enabling an optical measurement to be made through the transparent aperture.

In some embodiments, the sample or object holder comprises an access port, a reference surface, and two or more actuated arms (e.g., clamps). The arms have the dual function of a) pushing a sample or object towards the center of the holder and b) clamping a sample or object in place. The object is placed via the access port onto the reference surface anywhere within an open area of the access port.

In some embodiments, the reference surface is an optically transparent plate. In some embodiments, the reference surface comprises one or more actuated plates. In some embodiments, the sample or object holder comprises one or more actuation mechanism. In some embodiments, one or more actuation mechanisms of the sample or object holder comprise manual actuator(s).

In some embodiments, clamping arms of the sample or object holder have common actuation on OPEN but have independent actuation (e.g., via separate torsion springs) for actuation to CLOSE.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A sample holder, comprising:
   a bottom, wherein the bottom has an upper surface comprising an initial area for supporting a sample, wherein supporting the sample comprises holding the sample in a z-direction;
   one or more arms, wherein the one or more arms actuate to move the sample from an initial location in the initial area to a target area and hold the sample in the target area; and
   an actuation device for actuating the one or more arms, wherein the actuation device comprises a cover rotatably movable between a first position and a second position, wherein moving the cover to the first position actuates the one or more arms to move to a default position, and wherein moving the cover to the second position actuates the one or more arms to move to an actuated position holding the sample in the target area.

2. A sample holder as in claim 1, further comprising one or more bottom actuators, wherein the one or more bottom actuators moves the bottom to provide optical access to the sample.

3. A sample holder as in claim 2, wherein the bottom no longer supports the sample when optical access is provided to the sample.

4. A sample holder as in claim 2, wherein the one or more arms and the one or more bottom actuators are both actuated using the actuation device.

5. A sample holder as in claim 4, wherein the one or more arms are actuated first to hold the sample and then the one or more bottom actuators are actuated to remove the bottom.

6. A sample holder as in claim 4, wherein the one or more bottom actuators are actuated first to replace the bottom and then the one or more arms are actuated to release the sample.

7. A sample holder as in claim 1, wherein the actuation device is actuated by manually twisting the cover.

8. A sample holder as in claim 1, wherein the bottom comprises one or more plates.

9. A sample holder as in claim 1, wherein the bottom comprises a transparent plate to provide optical access to the sample.

10. A sample holder as in claim 1, wherein the bottom comprises an aperture to provide optical access to the sample.

11. A sample holder as in claim 1, wherein holding the sample in the target area comprises not allowing the sample to move in the x-y plane.

12. A sample holder as in claim 1, wherein holding the sample in the target area comprises not allowing the sample to move in the z plane.

13. A sample holder as in claim 1, wherein the one or more arms comprises three or four arms.

14. A sample holder as in claim 1, wherein the one or more arms comprises ledges to support the sample.

15. A sample holder as in claim 1, wherein the one or more arms sweep the initial area to move the sample to the target area.

16. A sample holder as in claim 1, wherein the target area comprises an area where the sample is optically measured.

17. A sample holder as in claim 1, wherein each of the arms is coupled to a torsion spring.

18. A sample holder as in claim 1, wherein the initial area is large enough to place and retrieve the sample by hand.

19. A sample holder as in claim 1, wherein the sample shape is one of the following: round, elliptical, oval, or oblong.

20. A sample holder as in claim 1, further comprising: one or more magnetic aligners, wherein the magnetic aligners align the sample holder to a sample reader.

21. A method of sample holding, comprising:
providing a bottom, wherein the bottom has an upper surface comprising an initial area for supporting a sample, wherein supporting the sample comprises holding the sample in a z-direction;
providing one or more arms, wherein the one or more arms actuate to move the sample from an initial location in the initial area to a target area and hold the sample in the target area; and
providing an actuation device for actuating the one or more arms, wherein the actuation device comprises a cover rotatably movable between a first position and a second position, wherein moving the cover to the first position actuates the one or more arms to move to a default position, and wherein moving the cover to the second position actuates the one or more arms to move to an actuated position holding the sample in the target area.

* * * * *